United States Patent [19]

Chamness

[11] Patent Number: 5,686,083
[45] Date of Patent: Nov. 11, 1997

[54] COMPOSITIONS FOR TREATING CORNS AND CALLUSES

[75] Inventor: Thomas W. Chamness, Memphis, Tenn.

[73] Assignee: Schering-Plough HealthCare Products Inc., Memphis, Tenn.

[21] Appl. No.: 514,444

[22] Filed: Aug. 11, 1995

Related U.S. Application Data

[63] Continuation of Ser. No. 351,967, Dec. 8, 1994, abandoned.

[51] Int. Cl.$^6$ ...................................................... A61K 7/00
[52] U.S. Cl. .......................... 424/401; 424/61; 424/274; 424/311; 424/642; 514/544
[58] Field of Search .......................... 424/401, 61, 402, 424/274, 78.03, 642; 514/846, 544, 859, 944, 936, 937, 938, 969, 946, 947

[56] References Cited

U.S. PATENT DOCUMENTS

| | | | |
|---|---|---|---|
| 3,920,835 | 11/1975 | Van Scott et al. | 424/311 |
| 3,984,566 | 10/1976 | Van Scott et al. | 424/283 |
| 4,234,599 | 11/1980 | Van Scott et al. | 424/279 |
| 4,363,815 | 12/1982 | Yu et al. | 424/274 |
| 4,568,539 | 2/1986 | Ashton et al. | 424/69 |
| 4,694,021 | 9/1987 | Schweiger | 514/544 |
| 4,699,924 | 10/1987 | Durrant et al. | 514/558 |
| 4,824,865 | 4/1989 | Bowser et al. | 514/558 |
| 5,091,171 | 2/1992 | Yu et al. | 424/642 |
| 5,176,916 | 1/1993 | Yamanaka et al. | 424/448 |
| 5,310,730 | 5/1994 | Funjinuma et al. | 514/35 |

FOREIGN PATENT DOCUMENTS

| | | |
|---|---|---|
| 919505 | of 1970 | Belgium . |
| 0086070 | 8/1983 | European Pat. Off. . |
| 0413528 | 2/1991 | European Pat. Off. . |
| 0508324 | 10/1992 | European Pat. Off. . |

OTHER PUBLICATIONS

Knood, Chemical Abstracts, vol. 91, #9505 (1978).

Primary Examiner—Thurman K. Page
Assistant Examiner—Sharon Howard
Attorney, Agent, or Firm—Matthew Boxer; John J. Maitner

[57] ABSTRACT

Topical compositions for the treatment of corns and calluses comprising a 4 carbon α-keto acid and a pharmaceutically acceptable carrier, are described.

8 Claims, No Drawings

COMPOSITIONS FOR TREATING CORNS AND CALLUSES

This is a continuation of application Ser. No. 08/351,957 filed Dec. 8, 1994, now abandoned.

BRIEF SUMMARY OF THE INVENTION

The invention relates to topical compositions for treating corns and calluses, which comprise a 4 carbon α-keto acid, most preferably α-ketobutyric acid; or its corresponding salts or esters in combination with a pharmaceutically acceptable carrier. The invention also relates to a method for treating the above-described conditions which comprises administering an effective amount of α-ketobutyric acid; or its corresponding salts or esters.

DETAILED DESCRIPTION OF THE INVENTION

Hyperkeratotic tissues, such as: corns (heloma) and calluses (tyloma) are well defined, thickened lesions of the epidermis. They occur at skin sites that are normally involved in chronic mechanical stress. Pain produced by the thickened tissue can cause these lesions to be debilitating.

Traditionally, "keratolytic agents", such as: salicylic acid and resorcinol, have been applied topically to these lesions to solubilize intercellular bonds resulting in desquamation of the thickened, hyperkeratotic tissues.

The goal was to develop a faster acting corn and callus remover product. To achieve this goal α-ketobutyric acid was evaluated. Assays of keratinocyte differentiation and keratolytic action, as described below were employed to identify the activities possessed by this compound.

The present invention provides new topical compositions for the treatment of all kinds of corns and calluses. The compositions of the invention provide for faster removal of corns and calluses than do prior art compositions. The invention also relates to a method for treating the above-described conditions which comprises administering an effective amount of a 4 carbon α-keto acid; or its corresponding salts or ester.

The topical compositions of the present invention comprise a 4 carbon α-keto acid most preferably α-ketobutyric acid; or its salts esters. As used herein, "a 4 carbon α-keto acid" means a 4 carbon straight or branched chained α-keto acid such as α-ketobutyric acid; or its salts or esters. The preferred α-keto acid of the invention is α-ketobutyric acid.

The chemical structure of α-ketobutyric acid is as follows:

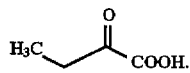

The topical compositions of the invention also comprise a pharmaceutical carrier material suitable for topical use.

A composition in accordance with the invention comprises α-ketobutyric acid in a range of about 2 to about 64% (weight/weight).

More preferably, the topical compositions of the invention contain α-ketobutyric acid at a range of about 4 to about 40% (weight/weight).

Those skilled in the art will be able to maximize the safety and efficacy of a given formulation. Compositions of the invention can take any of the following delivery forms: salves, lotions, plaster devices, collodion-type vehicles, suspensions, ointments, creams, gels, sprays, bandages, patches or other appropriate topical vehicles or delivery devices.

Topical compositions of the invention contain a pharmaceutically acceptable carrier. The pharmaceutically acceptable carrier delivers the active ingredient to the site of application. The pharmaceutically acceptable carrier may be a liquid such as propylene glycol, petrolatum, ethanol, acetone, dimethyl sulfoxide (DMSO), and the like. The pharmaceutically acceptable carrier may also be pad devices, disks or plaster. The pharmaceutically acceptable carrier may also be a film former such as flexible collodion, USP.

Topical compositions of the invention may also contain a viscosity enhancer. Viscosity enhancers increase the viscosity of the composition so that it does not spread beyond the site of application. An example of a viscosity enhancer is Balsam Fir (Oregon).

Topical compositions of the invention may also contain a film former. When a film former dries, it forms a protective film over the site of application to prevent removal of active ingredient from the site. An example of a film former which may be used is Flexible Collodion, USP.

Topical compositions of the invention may also contain a colorant such as β-Carotene.

Topical compositions of the invention may also contain a solvent which serves to dissolve the active ingredient. An example of a solvent which may be used is acetone. As can be seen, the solvent may also sometimes serve as the carrier.

In preparing topical compositions of the invention, there can be added conventional adjuvants such as propionic acid, propylene glycol, acetone and lactic acid, conventional penetration enhancers such as erucic acid, oleic acid, and behenic acid; conventional buffers, preservatives, hydrophilic emulsifiers, lipophilic emulsifiers, sun-screening agents, perfumes, emollients, deodorants, humectants, and the like. Colorants may also optionally be added in the compositions of the invention.

Current collodion-based FDA monograph approved formulas may be employed in such topical liquid compositions.

One skilled in the art, would be able to devise other suitable liquid formulations.

Alternatively, current plaster pad-type FDA monograph approved formulas may be used in devising compositions of the invention.

One skilled in the art would be able to devise a variety of suitable plaster pad-type formulations. Modified FDA monograph approved pad devices, disks or plaster may also be used as the carrier material. One skilled in the art would be able to apply α-ketobutyric acids to these pad devices, disks or plaster to form a composition of the invention.

Modified FDA monograph approved liquid vehicles may be used as the carrier material.

In preparing topical compositions of the invention, there can be added conventional adjuvants such as propionic acid, salicylic acid, propylene glycol, acetone and lactic acid, conventional penetration enhancers such as erucic acid, oleic acid, and behenic acid; conventional buffers, preservatives, hydrophilic emulsifiers, lipophilic emulsifiers, sun-screening agents, perfumes, emollients, deodorants, humectants, and the like.

In applying liquid formulations to the patient in need of such treatment, liquid formulations are applied, rubbed or spread on the affected area of the skin.

In applying plaster-pad formulations to the patient in need of such treatment, plaster-pad formulations are applied to the affected area of the skin so that the pad adheres to the skin.

Compositions of the invention are to be applied in a therapeutically effective amount. A "therapeutically effective amount" means any amount which will cause improvement in a disease condition (such as removal of a callus) when applied to the affected area repeatedly over a period of time. The amount will vary with the condition being treated and the concentration of the active ingredients in the formulation being applied. Appropriate amounts in any given instance will be readily apparent to those skilled in the art by routine experimentation.

As used herein, α-KBA refers to α-ketobutyric acid, and SA refers to salicylic acid.

RESULTS OF IN VITRO STUDIES

The following sections summarize the results of the in vitro and in vivo studies that were performed to compare the effects of α-KBA and SA on several cellular processes involved in keratinocyte differentiation. These data suggest that the keratolytic action of SA is linked to its activity in stimulating keratinocyte differentiation processes. Processes of keratinocyte differentiation that were analyzed in these studies included: 1. DNA synthesis inhibition, 2. Apoptosis, 3. Intracellular calcium flux, 4. Cellular envelope formation, 5. Desmosome degradation, and 6. Plasminogen activator expression.

These six parameters represent integral processes involved in terminal differentiation of keratinocytes that may be involved in the normalization that occurs when cornified tissue is treated with keratolytic agents. These differentiation processes are activated during the transition phase of epidermal development resulting in the genesis of corneocytes for formation of the stratum corneum and normal desquamation of corneocytes for the skin's surface. Compounds that activate keratinocyte differentiation processes are believed to be more effective keratolytic agents. In many cases α-KBA caused greater effects on the differentiation processes listed above than did SA. However, the effects were not always toward increased differentiation.

1 Effects of α-KBA and SA on Inhibition of DNA Synthesis

Inhibition of DNA synthesis in keratinocytes is believed to play a role in treating hyperkeratotic conditions such as psoriasis, corns and calluses. [Hegemann, L., B. Bonnekoh, L. A. A. van Rooijen and G. Mahrie. Antiproliferative effects of protein kinase C inhibitors in human keratinocytes. J Dermatol Sci 4:18 –25, 1992. Weirich, E. G., J. K. Longauer and A. H. Kirkwood. Epidermal antihyperplastic effects of contact antiphlogistics. Dermatologica 156:1 –7, 1978]. Inhibiting keratinocyte proliferation is believed to aid in reversing abnormal hyperproliferative effects in these tissues. Experiments were conducted on third passage NHEK cells treated with α-KBA or SA to determine inhibition of DNA synthesis as measured by incorporation of tritiated ($^3$H-) thymidine. Triplicate wells of NHEK cells grown in 6-well trays were used per treatment group. The cells were simultaneously pulsed with $^3$H-thymidine and the test compound and allowed to incubate overnight (18 hours). Following this treatment, the cells were harvested and the $^3$H-thymidine taken up by the cells was measured by liquid scintillation counting. α-KBA caused a 57% inhibition of $^3$H-thymidine uptake compared to the ethanol vehicle control, while SA caused a 50% inhibition versus the control. When both compounds were tested at 20 mM concentrations, α-KBA and SA caused a similar decrease in proliferation in NHEK cells by this in vitro method.

2 Effects of α-KBA and SA on Apoptosis

Apoptosis is the programmed or gene-controlled process of cell death. It is believed to be a factor in regulating normal differentiation of the skin and other tissues [Haake, A. R. and R. R. Polakowska. Cell death by apoptosis in epidermal biology. J. Invest Dermatol 101:107–112, 1993]; and may affect desquamation [Pause, R., T. Resonate, N. Haas and B. M. Czarnetzki. Patterns of Cell death: the significance of apoptosis for dermatology. Exp Dermatol 2:3–11, 1993.] Apoptosis may be a part of the normal transition of keratinocytes to corneocytes that occurs in the stratum granulosum, a process that is altered in corns. Apoptosis experiments were performed in vitro using normal human epidermal keratinocytes (NHEK) or squamous cell carcinoma cells (SCC-9) in cell culture. The following protocol was used for these experiments: $3+10_6$ cells were treated for four days with 10 mM of either α-KBA or SA in medium containing a final concentration of 1.5 mM calcium. DNA was then extracted from the treated cells for analysis. Apoptosis was determined by measuring DNA fragmentation using agarose gel electrophoresis. A subjective scale for measuring the degree of apoptosis, termed the Apoptosis Factor, was used to score the results from the gel electrophoreses patterns. This subjective scale used A23187, a calcium ionophore, as the positive control, thus the effects of α-KBA and SA were compared to those of A23187 for the induction of DNA fragmentation. Based on this analysis it was determined that α-KBA has an apoptosis factor of 2 compared to a relative apoptosis factor of 1 for SA. In comparison, the positive control A23187 has an apoptosis factor of 4. Thus, α-KBA caused a higher amount of DNA fragmentation in this model when compared with SA.

3 Effects of α-KBA and SA on intracellular Calcium Flux

Increased intercellular calcium levels are known to initiate keratinocyte differentiation [Eckert, R. L. Structure, function, and differentiation of the keratinocyte. Physiological Rev 69:1316–1347, 1989]. Measurement of intracellular calcium flux is a key in vitro test that can be used to evaluate differentiation related events in keratinocytes that may influence desquamation of hyperkeratotic tissue. The intercellular calcium flux experiments were conducted as follows: $3+10^6$ cells (NHEK or SCC-9) were loaded with Indo-1 AM, a calcium chelating dye. Prior to treatment with either α-KBA or SA, the cells were suspended in 1.5 mM calcium assay buffer at a density of $1+10^6$ cells/ml. An aliquot of the keratolytic compound was added to a quartz cuvette containing 3 ml of the cell suspension and mixed. Calcium flux was determined by an increase in the relative fluorescence in the treated cells measured by a Shimadzu spectrofluorophotometer. Both α-KBA and SA cause increased intracellular calcium flux. Based on levels of cell fluorescence measured in this assay of calcium flux α-KBA caused an increase of 33 relative fluorescence units (RFU), compared to 100 RFU for SA. Interestingly, α-KBA also increases intracellular calcium flux at 10 μM concentration. In comparison, SA has the ability to achieve a higher RFU, however, it requires an order of magnitude 1000 times greater in concentration (10 mM) than that needed by α-KBA. Therefore, α-KBA appears to be efficient in increasing intracellular calcium flux when compared with SA in vitro.

4 Effects of α-KBA and SA on Cross-linked Cellular Envelope Formation

Keratinocytes undergo terminal differentiation to become corneocytes, which form the stratum corneum layer of the epidermis. Corneocyte generation is a programmed process with recognized biochemical and morphological changes to the keratinocytes that include: reorganization of intermediate keratin filaments, accumulation of keratohyalin granules, production of certain lipids, and the formation of the cross-linked cellular envelope (CE). During the late stages of keratinocyte terminal differentiation, the highly insoluble, cross-linked protein CE is formed on the inner aspect of the cell's plasma membrane. Through the action of a plasma membrane associated, CE precursor proteins, such as loricrin and involucrin are cross-linked by $\epsilon$-($\gamma$-glutamyl) lysine bonds to form this specialized corneocyte structure. Since CE formation is a unique marker of terminally differentiated keratinocytes, an in vitro assay of CE induction was used to measure and compare the keratinocyte differentiation inducing potential of $\alpha$-KBA and SA.

The scattering of light emitted at 340 nm was used as a relative measurement of CE formation. Data is presented as the mean $\pm$S.E.M. absorption ($A_{340}$) value for each of the test groups. CE were induced in SCC-9 cells by treating them with 10 mM SA or 10 mM $\alpha$-KBA. SA produced about twice as many CE as $\alpha$-KBA under these test conditions, where as $\alpha$-KBA produced almost twice as much CE as the 1% (v/v) ethanol vehicle control. $\alpha$-KBA therefore has the ability to stimulate the production of CE in vitro but not to the same degree as SA.

5 Effects of $\alpha$-KBA and SA on Desmosome Degradation in Organ-cultured Normal Human Breast Skin Desmoglein is a component of desmosomes, the adhesion molecules of the epidermal keratinocytes. Degradation of desmosomes in the epidermis increases desquamation of the tissue [Lundstrom, A. and T. Egelrud. Evidence that cell shedding from plantar stratum corneum in vitro involve endogenous proteolysis of desmosomal protein desmoglein I. J Invest Dermatol 94:216–220, 1990]. This process is believed to be important in chemical corn removal and the normalization of hyperkeratotic tissue. Desmoglein expression in tissue samples can be visualized by light microscopy using immunohistochemical staining methods. In the organ culture model, normal human breast skin was treated with 15 mM of either $\alpha$-KBA or SA for 24 hours. Following this treatment, frozen sections of the tissues were made and stained by indirect immunoperoxidase using a primary anti-desmoglein monoclonal antibody. Hematoxylin and eosin sections of the tissues were also made. Compared to control tissue sections, there was reduced anti-desmoglein staining observed in the skin treated with $\alpha$-KBA indicating that this compound caused a decrease in the expression of desmoglein. SA caused a more significant reduction of the intensity of desmoglein staining than $\alpha$-KBA. In conclusion, both $\alpha$-KBA and SA can effect degradation but SA is capable of doing so to a greater extent.

6 Effect of $\alpha$-KBA and SA on Plasminogen Activator Expression

Plasminogen activators (tissue-type, tPA; and urokinase-type, uPA) convert plasminogen to plasmin an active serine proteinase that can degrade desmosomes. This activity of plasmin is believed to play a role in desquamation of hyperkeratotic tissue [Lazarus, G. S. and P. J. Jensen. Plasminogen activators in epithelial biology. Sem Thromb Hemostasis 17:210–216, 1991.]. The activity of tPA and uPA is regulated by plasminogen activator inhibitor type-1 (PAI-1) and plasminogen activator inhibitor type-2 (PAI-2). A study was conducted using polymerase chain reaction (PCR) analysis to measure the expression of PA and PAI mRNA levels in in vivo SA treated corn tissue and untreated corn tissue. The following results were obtained from that study. Compared to normal skin, untreated corns displayed a higher level of mRNA for PAI-2 and decreased amount of mRNA for tPA. SA treated corns showed an increase in tPA expression and a concomitant decrease in PAI-2 compared to the untreated corn samples. The level of tPA and PAI-2 gene expression in SA treated corns was equivalent to that observed in normal skin. This study demonstrates a probable key relationship for enhanced protease activity and concomitant decrease of inhibitor activity in keratolytic agent induced desquamation of corn tissue.

In vitro studies with SCC-9 cells were also conducted to determine the effects of $\alpha$-KBA and SA on the gene expression of tPA, uPA, PAI-1 and PAI-2. SCC-9 cells were treated with 5 mM $\alpha$-KBA for 48 hours. Total RNA was extracted and processed for PCR analysis to amplify mRNA for the PAs and PAIs. The test samples with appropriate controls from the PCR analysis were run on agarose gels to determine the level of gene expression. There was a slight up-regulation of tPA gene transcripts in cells treated with $\alpha$-KBA compared to controls. None of the other genes evaluated appeared to be affected by treatment with $\alpha$-KBA. Similar to the untreated control, SA had no effect on modulating the gene expression of either PAs or PAIs, in vitro. However, in this experiment both tPA and uPA mRNA levels were increased in SCC-9 cells treated with ethanol. In summary, $\alpha$-KBA but not SA causes a slight up-regulation of tPA mRNA expression in SCC-9 cells, suggesting a mechanistic role in keratolysis.

Conclusions From The In Vitro Studies

In comparative studies, it was shown that $\alpha$-KBA, like SA, exerted important effects on certain keratinocyte differentiation processes. For example, $\alpha$-KBA enhanced degradation of desmosomes, blocked keratinocyte proliferation, induced apoptosis, stimulated intracellular calcium flux, induced CE formation and induced tPA gene expression. Based upon this activity, it is believed that $\alpha$-KBA is useful as a keratolytic agent.

Description of Methods and Results of Guinea Pig Footpad Assays

Analysis of callus removal were performed according to the following protocol using the guinea pig footpad as the test site. Three Hartley guinea pigs (250–400 g) were used per test group for in vivo evaluations. Either the right or left footpads were treated with the opposite footpad serving as the untreated control. For each treatment group, the same footpad was treated on each animal. The treated footpad received 200 µl of the test material saturated into a small cotton pledger. The cotton pledger was immediately placed on the guinea pig's footpad and occluded with several wrappings of Blenderm tape (3M Corporation, St. Paul, Minn.) and finally secured from removal with a wrapping of Zonas tape (Johnson and Johnson, New Brunswick, N.J.). Each group of three animals was placed in a polycarbonate cage with contact bedding for 18–24 hours (overnight). At the end of the treatment period, the bandages were removed with surgical scissors and the footpads were examined for gross keratolytic effects and dermatoxicity. Observations were carried out at daily intervals for one week. Clinical grades were recorded for possible keratolytic effects beginning on Day 2 (48 hours post-treatment) and continuing through Day 7. Appropriate vehicle controls and bandage control groups were included in each experiment. $\alpha$-KBA (Sigma Chemical Co., St. Louis, Mo.) was prepared as a 12%, 9% or 5% (w/w) solution in the same liquid vehicle (Table I) that is used for the currently marketed, FDA monograph approved Dr. Scholl's Liquid Corn/Callus Remover™ that contains SA at 12.6% (w/w).

TABLE I

Liquid Formula for Evaluating α-Ketobutyric Acid in the GPFA.

| Component | Percentage of Formula (% w/w/) |
| --- | --- |
| α-Ketobutyric Acid | 12.00, 9.00 or 5.00[1] |
| Balsam Fir (Oregon) | 5.00 |
| β-Carotene, 22% HSR in Vegetable Oil[2] | 0.01 |
| Acetone | 10.00 |
| Flexible Collodion, USP | q.s. 100.00 |

[1]Three different concentrations of α-KBA in liquid collodion vehicle were evaluated in the GPFA, that is, 12%, 9% and 5%.
[2]β-carotene was optionally used in some of the test formulations. In those formulations in which it was not used, the difference was made up with flexible collodion U.S.P.

The relative efficacy of keratolytic action of these compounds for removal of guinea pig footpad callus was determined by the following clinical grading scale:

| Clinical Grade | Appearance of Footpad and Callus |
| --- | --- |
| 0 | No visible difference, equal to control. |
| 0.5 | Slight fine cracks in skin visibly different from control |
| 1 | Somewhat larger cracks with edges turned up slightly. |
| 2 | Obvious separation of the stratum corneum (SC) over a limited area of the footpad. |
| 3 | Separation of the SC over a large area of the footpad. |
| 4 | SC has peeled off completely revealing intact underlying epidermis. |

The clinical grades were then used to calculate a keratolytic efficacy score referred to as the Keratolytic Index (KI). The following formula was used to calculate the KI for a given test group:

$$KI = \frac{\text{Maximum Average Daily Clinical Grade}}{\text{The Number of Days Until}} \times 10$$
$$\text{The Average Clinical Grade Equals 2}$$

TABLE II

Keratolytic Indices (KIs) for α-Ketobutyric Acid and Salicylic Acid Determined in the Guinea Pig Footpad Assay.

| Keratolytic Agents | Percent (w/w) of Keratolytic Agent in Formula[1] | N[2] | KI[3] |
| --- | --- | --- | --- |
| EXPERIMENT 1 | | | |
| Salicylic Acid | 12.0 | 3 | 3.9 |
| α-Ketobutyric Acid | 12.0 | 3 | 12.2 |
| EXPERIMENT 2 | | | |
| Salicylic Acid | 12.0 | 3 | 2.9 |
| α-Ketobutyric Acid | 9.0 | 3 | 7.8 |
| α-Ketobutyric Acid | 5.0 | 3 | 3.3 |

[1]Percent (w/w) of the active keratolytic agent in liquid collodion vehicle.
[2]N refers to the number of guinea pigs tested in each group.
[3]KI refers to the mean KI for the experiment reported. The mean KI of combined vehicle control groups was less than 1.

The KI scores achievable for this method range from 0, no apparent effect, to 20, maximum keratolytic action. The cumulative results of these analyses, comparing α-KBA and SA are given in Table II. As shown in Experiment 1 of Table II, α-KBA at 12%, was clearly more effective (KI=12.2) than SA at 12.0% (KI=3.9). Likewise, in Experiment 2 of Table II, α-KBA at 9% but not 5% was more effective (i.e., KI=7.8 and KI=3.3, respectively) than SA at 12% (KI=2.9). By molar equivalency 9% α-KBA is nearly equal to 12% SA.

Using a modified application protocol the KI scores for 9% and 5% α-KBA were found to be nearly equivalent (Table III). In this study the test materials were applied (30 μl) directly to the guinea pig footpad calluses on 3 consecutive days. Scoring of callus removal, beginning in day 2 of the assay, was the same as that described above. Under these assay conditions the degree and rate of callus removal by α-KBA were similar for 9% (KI=6.0) and 5% (KI=5.3) solutions. Both concentrations of α-KBA were more effective than 12% SA (KI=1.9) when applied directly to the guinea pig footpad callus.

TABLE III

Keratolytic indices (KIs) for α-Ketobutyric Acid and Salicylic Acid Determined in a Modified Guinea Pig Footpad Assay.

| Keratolytic Agents | Percent (w/w) of Keratolytic Agent in Formula[1] | N[2] | K[13] |
| --- | --- | --- | --- |
| Salcylic Acid | 12.0 | 3 | 1.9 |
| α-Ketobutyric Acid | 9.0 | 3 | 6.0 |
| α-Ketobutyric Acid | 5.0 | 3 | 5.3 |

[1]Percent (w/w) of the active keratolytic agent in liquid collodion vehicle.
[2]N refers to the number of guinea pigs tested in each group.
[3]KI refers to the mean KI for the experimental group indicated. The mean KI of combined vehicle control groups was less than 1.

Summary of Histopathology Study

The higher KI score indicates that 12%, 9% and 5% α-KBA had stronger keratolytic effects on guinea pig footpad callus removal than did 12% SA. Although the stratum corneum of the callus was readily separated from the guinea pig footpad, there was no histological evidence of significant damage to epidermal or dermal structures in footpads treated for 48 hours with 12%, 9% and 5% α-KBA. Conversely, the appearance of the SA treated tissue showed marked pathological changes compared to that of the vehicle control. At 100× magnification the basal, parabasal and spinous layers in α-KBA treated footpads appeared normal. Compared with normal tissue, there were fewer layers of stratum granulosum and more diffuse keratohyalin granules in α-KBA treated footpads. The size of the keratinocyte nuclei decreased progressively from the stratum basal through the stratum spinosum layers of both α-KBA treated and normal footpads. However, the extent of nuclear degradation was greater in the upper layers of the spinosum of α-KBA treated footpads. Normal chromatin staining of the nuclei was observed in the basal and parabasal layers of these tissues. α-KBA treatment caused sloughing of the outer ⅔ of the stratum corneum, which was separated from the underlaying footpad. Although the collagen was less compact in the α-KBA treated tissue compared to normal, it was not significantly different from that of SA treated footpads. There was no evidence of inflammation in the dermis of the α-KBA treated footpads. At 160× and 400× magnification the corneocytes adjacent to the stratum granulosum were "nucleated", that is contained remnants of chromatin. This later finding, however, was not observed in biopsies of α-KBA treated footpads taken from other animals.

In contrast, significant histological alterations, dissimilar to those caused by α-KBA, were observed in guinea pig footpads treated for 48 hours with 12% SA. At 100× magnification the basal and parabasal layers were disorganized in appearance compared to normal tissue. There was a loss of nuclei in many cells in the upper layers of the stratum spinosum. In the superficial layers of the stratum spinosum there was marked acantholysis, with significant tissue separation. Keratohyalin staining was faint in the stratum granulosum. The stratum granulosum layer was difficult to distinguish. Dermal collagen appeared more diffuse than normal, but there was no evidence of inflammation in the dermis. At 160× magnification there were marked signs of acantholysis. At 400× magnification the stratum corneum appeared very compact, there was a reduced number of keratohyalin granules in the stratum granulosum, many nuclei were condensed or lost from the upper and parabasal layers of the stratum spinosum. In one section of the tissue taken near the edge of treated and untreated callus a "tongue" of new epidermis appeared to be growing into and underneath the tissue treated with SA, evidence of wound repair processes. Thus, the histological alterations in guinea pig footpads associated with SA treatment appeared more severe than those caused by α-KBA or was observed in the human corns treated with SA.

Effects of α-KBA and SA on the Expression of Desmosomal Proteins in the Epidermis of Guinea Pig Footpads.

Biopsies were taken from guinea pig footpads 48 hours after treatment with α-KBA or SA. The tissues were processed for indirect immunoperoxidase staining of desmosomes using monoclonal antibodies against human desmoglein (DG) and desmoplakin (DP). As shown, SA caused a decrease in the level of DG expression. In comparison, α-KBA had much less effect on DG expression. The expression of DP was reduced in both SA and α-KBA treated footpads. There appeared, however, to be less immunoperoxidase staining in the transition layers of α-KBA treated guinea pig footpads than was observed in the SA treated tissues. These results are similar to those obtained from examination of SA-treated human hard corns in which a reduced level of desmosomes was observed.

Conclusions From The Animal Studies

The results of the GPFAs indicate that α-KBA has stronger keratolytic action than SA for mediating guinea pig footpad callus removal. This finding is consistent with the results of our in vitro studies, summarized above, showing α-KBA was as effective or more effective than SA in stimulating certain processes involved in keratinocyte differentiation.

Interestingly, the stronger keratolytic activity of α-KBA did not result in any adverse tissue damage beyond that which is acceptable for approved keratolytic agents, such as SA.

Ingredients of preferred compositions of the invention fall within the following ranges:

| Component | Percentage of Formula % (weight/weight) |
| --- | --- |
| α-ketobutyric acid | 2–40 |
| Balsam Fir (Oregon) | 1–10 |
| β-Carotene, 22% in Vegetable Oil | 0–0.1 |
| Acetone | 10–20 |
| Flexible Collodion, USP | 50–80 |

| Component | Percentage of Formula % (weight/weight) |
| --- | --- |

Examples of compositions of the invention are as follows:

Example 1

| Component | Percentage of Formula % (weight/weight) |
| --- | --- |
| α-ketobutyric acid | 9 |
| Acetone | 10 |
| Flexible collodion (USP) | 81 |

The above composition containing 9% α-KBA was made as follows:
1. The α-KBA was placed in a suitable vessel.
2. Acetone was added to the α-ketobutyric acid in the vessel and mixed until a solution was formed.
3. To the mixture formed in step 2, flexible collodion was added to reach the desired final volume and mixed until the entire contents were thoroughly mixed.
4. The composition was transferred to appropriate containers for storage in a standard, explosion proof freezer (−10° to −20° C.).

Example 2

| Component | Percentage of formula % (weight/weight) |
| --- | --- |
| α-ketobutyric acid | 9 |
| Acetone | 10 |
| Dipropylene Glycol | 81 |

The above composition was made as follows:
1. The α-KBA was placed in a suitable vessel.
2. Acetone was added to the α-ketobutyric acid in the vessel and mixed until a solution was formed.
3. To the mixture formed in step 2, dipropylene glycol was added to reach the desired final volume. These materials were mixed thoroughly.
4. The composition was transferred to appropriate containers for storage in a standard, explosion proof freezer (−10° to −20° C.).

Example 3

| Component | Percentage of formula % (weight/weight) |
| --- | --- |
| α-ketobutyric acid | 9.0 |
| Acetone | 10.0 |
| Flexible collodion (USP) | 75.9 |
| Balsam fir (Oregon) | 5.0 |
| β-Carotene HSE 22% in vegetable oil | 0.1 |

The above composition containing 9% α-KBA was made as follows:
1. The α-KBA was placed in a suitable vessel.
2. Acetone and flexible collodion was added to the α-ketobutyric acid in the vessel and mixed until a solution was formed.
3. To the mixture formed in step 2, balsam fir and β-carotene was added to reach the desired final volume and mixed until the entire contents were thoroughly mixed.

4. The composition was transferred to appropriate containers for storage in a standard, explosion proof freezer (−10° to −20° C.).

The most preferred compositions of the invention are:

4% α-ketobutyric acid

| | % W/W |
|---|---|
| Part A: | |
| α-ketobutyric acid (includes 10% coverage) | 4.40 |
| Acetone, NF | 10.00 |
| Flexible Collodion, USP | 80.60 |
| Part B: | |
| Balsam Fir Oregon | 5.00 |

Procedure:

1. α-ketobutyric acid was added to the acetone and Flexible Collodion of Part A and mixed until dissolved. This phase was manufactured in a glass bottle with a tight closure. Evaporation of the ingredients was avoided as much as possible.
2. Balsam Fir Oregon of Part B was added and mixed until uniform.
3. The material was stored in a freezer in a closed container, to avoid evaporation of the ingredients and to protect from light.
4. The material was packaged in ⅓ oz glass bottles. Packaged bottles should also be stored in a freezer.

9% α-ketobutyric acid

| | % W/W |
|---|---|
| Part A: | |
| α-ketobutyric acid (includes 10% coverage) | 9.90 |
| Acetone, NF | 10.00 |
| Flexible Collodion, USP | 75.10 |
| Part B: | |
| Balsam Fir Oregon | 5.00 |

Procedure for making the composition:

1. α-ketobutyric acid was added to the Acetone and Flexible Collodion of Part A and mixed until dissolved. This phase was manufactured in a glass bottle with a tight closure. Evaporation of the ingredients was avoided as much as possible.
2. Balsam Fir Oregon of Part B was added and mixed until uniform.
3. The resulting material was stored in a closed container in a standard, explosion proof freezer (−10° to −20°C.), to avoid evaporation of the ingredients and protect the material from light.
4. The resulting material was packaged in ⅓ oz glass bottles. Packaged bottles should also be stored in a freezer.

What is claimed is:

1. A composition comprising a 4 carbon α-keto acid in a range of about 2 to about 64% (weight/weight) and flexible collodion, USP.

2. A composition in accordance with claim 1 comprising on a weight/weight basis:

| Component | Percentage of Formula % (weight/weight) |
|---|---|
| α-ketobutyric acid | 2–40 |
| Balsam Fir (Oregon) | 1–10 |
| β-Carotene, 22% in Vegetable Oil | 0–0.1 |
| Acetone | 10–20 |
| Flexible Collodion, USP | 50–80 |

3. A topical composition in accordance with claim 1 comprising on a weight/weight basis:

| Component | Percentage of formula % (weight/weight) |
|---|---|
| α-ketobutyric acid | 9.9 |
| Acetone | 10.0 |
| Flexible collodion (USP) | 75.1 |
| Balsam fir (Oregon) | 5.0 |

4. A topical composition in accordance with claim 1 comprising on a weight/weight basis:

| Component | Percentage of Formula % (weight/weight)) |
|---|---|
| α-ketobutyric acid | 4.4 |
| Balsam Fir (Oregon) | 5.0 |
| Acetone | 10.0 |
| Flexible Collodion, USP | 80.6 |

5. A topical composition in accordance with claim 1 comprising on a weight/weight basis:

| Component | Percentage of formula % (weight/weight) |
|---|---|
| α-ketobutyric acid | 9.0 |
| Acetone | 10.0 |
| Flexible collodion (USP) | 75.9 |
| Balsam fir (Oregon) | 5.0 |
| β-Carotene HSE 22% in vegetable oil | 0.1 |

6. A topical composition in accordance with claim 1 comprising on a weight/weight basis:

| Component | Percentage of formula % (weight/weight) |
|---|---|
| α-ketobutyric acid | 9 |
| Acetone | 10 |
| Flexible collodion (USP) | 81 |

7. A method for removing corns and calluses which comprises topically administering a therapeutically effective amount of a composition defined in claim 1.

8. A composition comprising a 4 carbon α-keto acid in a range of about 2 to about 64% (weight/weight), acetone, and dipropylene glycol.

* * * * *